(12) United States Patent
    Tsoukalis

(10) Patent No.: US 8,882,707 B2
(45) Date of Patent: Nov. 11, 2014

(54) FLUIDS EXCHANGING SYSTEM FOR MEDICAL USE

(75) Inventor: Achilleas Tsoukalis, Anavyssos Attiki (GR)

(73) Assignee: MICREL Medical Devices S.A., Gerakas (GR)

( * ) Notice: Subject to any disclaimer, the term of this patent is extended or adjusted under 35 U.S.C. 154(b) by 0 days.

(21) Appl. No.: 13/431,362

(22) Filed: Mar. 27, 2012

(65) Prior Publication Data

US 2012/0289895 A1    Nov. 15, 2012

(30) Foreign Application Priority Data

Mar. 28, 2011 (GR) ................................. 110100184

(51) Int. Cl.
    *A61M 1/00*     (2006.01)
    *A61N 1/30*     (2006.01)
    *A61M 25/00*    (2006.01)

(52) U.S. Cl.
    CPC ... *A61M 25/0075* (2013.01); *A61M 2025/0031* (2013.01); *A61M 2025/0046* (2013.01); *A61M 2202/0464* (2013.01); *A61M 1/0084* (2013.01); *A61M 2025/0042* (2013.01); *A61M 2025/0002* (2013.01)
    USPC .............................. 604/118; 604/19; 604/119

(58) Field of Classification Search
    CPC .................. A61M 1/0058; A61M 2025/0057; A61M 1/0047; A61M 25/007
    USPC ..................... 604/19, 131, 118–121
    See application file for complete search history.

(56) References Cited

U.S. PATENT DOCUMENTS

| | | | |
|---|---|---|---|
| 3,965,901 A * | 6/1976 | Penny et al. | 604/119 |
| 4,536,179 A * | 8/1985 | Anderson et al. | 604/266 |
| 5,441,481 A | 8/1995 | Mishra et al. | |
| 6,669,679 B1 * | 12/2003 | Savage et al. | 604/500 |
| 7,780,638 B1 * | 8/2010 | Deniega et al. | 604/264 |
| 8,257,306 B2 * | 9/2012 | Grathwohl | 604/118 |
| 8,684,967 B2 * | 4/2014 | Engel et al. | 604/129 |
| 2006/0184098 A1 | 8/2006 | Barnitz et al. | |
| 2006/0247553 A1 | 11/2006 | Diermann et al. | |
| 2008/0200877 A1 | 8/2008 | Panotopoulos | |
| 2009/0054827 A1 * | 2/2009 | Eide | 604/9 |

OTHER PUBLICATIONS

European Search Report dated Sep. 18, 2012 from EP Application No. 12161696.5, 6 pages.

* cited by examiner

*Primary Examiner* — Nicholas Lucchesi
*Assistant Examiner* — Rebecca E Eisenberg
(74) *Attorney, Agent, or Firm* — Hollingsworth Davis, LLC

(57) ABSTRACT

A fluids exchanging system for medical use is provided. The system comprises an infusion pumping system, an aspiration pump, and an implantable catheter comprising a perforated dialysis cavity communicating with infusion and aspiration tubes in a communicating vessel manner. The implantable catheter further includes elastic holes.

18 Claims, 3 Drawing Sheets

FLUIDS EXCHANGING SYSTEM FOR MEDICAL USE

Solutions are known in the state of the art for the exchange of fluids in the body; however, the exchange of fluids in the brain needs a safety level that is not attained by them.

STATE OF THE ART

U.S. Pat. No. 4,694,832 Ungerstedt, EP0251512 Zako WO2007026182 Panotopoulos, U.S. Pat. No. 5,108,364 Takezawa, US20050020976 Maki Shin, U.S. Pat. No. 4,694,832, U.S. Pat. No. 4,755,175, U.S. Pat. No. 4,623,329, EP0321614, U.S. Pat. No. 6,454,740, WO2006054720.

There exists a great need for a reliable infusion system with the quasi-simultaneous suction of fluids in the body more specifically in the brain, wherein a large quantity of fluid is not feasible to be diluted using the existing in the market systems.

In the state of the art, Ungerstedt (U.S. Pat. No. 4,694,832) uses the micro-dialysis of fluids in a catheter via a membrane selective to the size of the molecules being exchanged through the natural equilibrium of the concentrations (dialysis), using only a single continuous flow pump for extracorporeal concentration measurement/analysis of these molecules. The single pump cannot be used in the brain for safety reasons (in our case vacuum), and the microporous membrane that it uses does not allow the transport of relatively large-sized waste material.

Zako (EP0251512) uses two synchronized, continuous flow pumps, measuring the intra-catheter pressure, in order to stop one or the other pump in case of either increased or low pressure.

Panotopoulos in WO2007026182 uses two pumps alternating in their operation, the one operating first, followed by a pause, the second operating thereafter, followed again by a pause, in order to provide a forced inward and/or outward flow. The pressure is programmed and there is no special provision for the detection of any blocking (not even a corresponding sensor inside the catheter), in which case the pumps continue to infuse and suck regularly but in short-circuit with blocked holes (the long exterior tubing helping in this case to collect sufficient fluid), without exchanging fluids with the body, thus endangering the patient. The reported measurement of cranial pressure is not used for any automatic unblocking action. Programming the pressure, instead of flow, derives from the exceptionally small cross-section of the holes (a few Dalton as in micro-dialysis) which is very difficult to regulate (via flow resistance), which in turn means the absence of provision for the suction of hematomas fragmented down to the size of 0.5 millimeters. Having holes of 0.5 mm in size, means that one cannot program pressure, only flow.

The transfer of large volumes of fluids in the brain is feasible using only (not forced) dialysis, or a lot of repeated small forced exchanges, in order not to increase the pressure in the cerebral cavity resulting in devastating effects.

The large volumes being exchanged present big benefits as well, i.e., rinsing of hematomas, surgical waste and destroyed cancerous regions. Safety requires the precision of the small volumes being exchanged as a first safety level for isobaric (in constant pressure) exchange, while in a second safety level, the pressure measurement inside the catheter should result initially in corrective actions, and in case the problem persists the sounding of an alarm.

In the literature (*Principles of Neurosurgery*/edited by Setti S. Rengachary, Robert H. Wilkins ISB 1-56375-022-8, 1994 Wolfe Publishing, chapter 2 page 2.3) it is reported that 1 ml of fluid does not alter the pressure inside the "brain and it may preferably comprise the maximum exchange quantity for this implementation.

In the state of the art, there is no catheter available that remains unblocked to the passage of the suction fluid waste, from the time it is first placed through surgery until the time it is connected to the circulating fluids system, as well as during its long term use for the large quantities reported above.

It is the intention of the present disclosure to present a catheter-pressure measurement programmed fluid circulation system possessing the necessary safety and reliability features for carrying out surgical procedures in the central nervous system and elsewhere.

BRIEF REFERENCE TO THE DRAWINGS

Figure 4A:
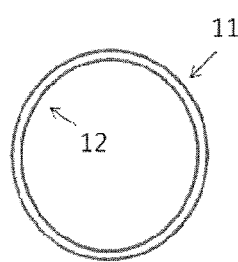
Figure 4B:
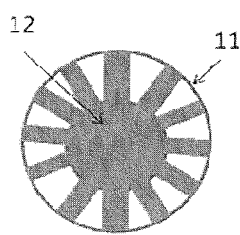

FIGS. 4A, B, C, show the preferred catheter internal structure.

Figure 5:
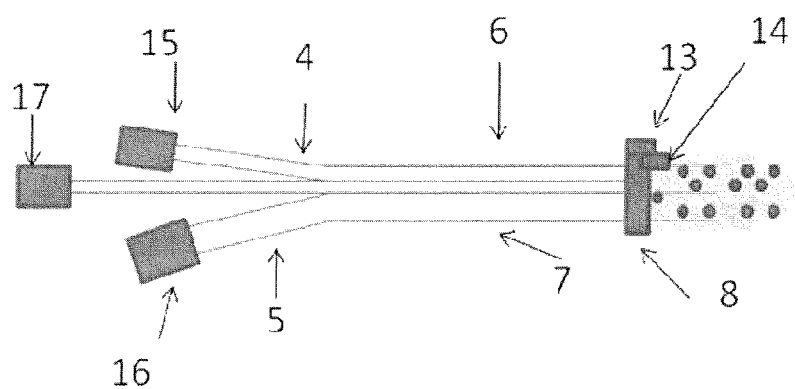

FIG. 5 shows an alternative embodiment of the catheter pumping system with the use of integrated pressure sensors.

Figure 6:
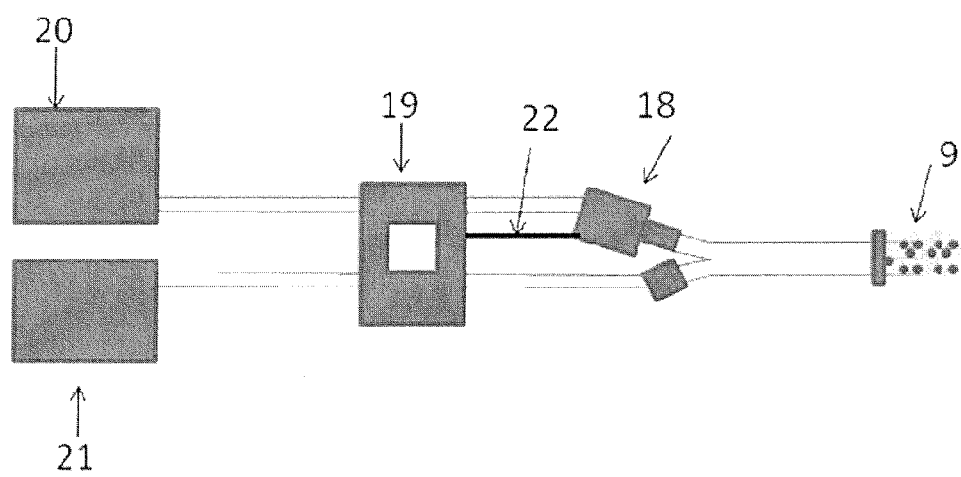

FIG. 6 shows another embodiment of the catheter pumping system with an external pressure sensor.

CATHETER DESCRIPTION

As shown in FIGS. 3 to 6, according to various embodiments, there is provided a catheter with one more infusion tubing 4 and a suction tubing 5 terminating inside a small common perforated "dialysis cavity" 9 at the catheter tip, such that even a small increase of (1 ml) in the infusion volume inside the catheter generates an exceedingly high unblocking pressure in order to remove any obstruction present. As further shown in FIGS. 3 and 5, the catheter additionally comprises an elastic hydraulic insulating clamp 8 connecting a main membrane casing 11 (cf. FIGS. 4A to 4C) of the dialysis cavity 9 with a conduit for fluid transport in a fluid-tight manner so as to prevent leaks of the dialysis cavity 9 even under high pressure.

The perforation of the dialysis cavity 9 is used for the low flow rate per hole in suction, in order to prevent the occlusion of the holes. Furthermore, the flow of fluid never stops, either outwards or inwards, in order to prevent occlusion of the holes that would be devastating for the treatment.

Moreover there may be a corrective infusion, using the intra-catheter pressure for obstruction indication to trigger the correction.

Elastic holes 10 in the perforated casing of the dialysis cavity 9 are provided, said holes 10 being pressure-dilated in order to release the entrapped material fragments and remove them using fluid pressure either outwards (infusion pressure) or inwards (negative aspiration pressure).

The dialysis cavity, through the holes, equilibrates the concentrations in a common dialysis of the fluids found inside and outside the dialysis cavity; this is combined with forced flow alternating in both directions, in order to achieve unblocking during infusion and an even suction of viscous and insoluble masses like pus etc.

Said dialysis cavity 9 is as small as possible in volume with an even smaller elastically varied volume, in such a way that the reversible volume being lost through diffusion and going straight to the suction during the switch in the direction of flow (hydraulic short-circuit) is much smaller than the volume of the stepwise infusion (preferably 1 ml in the brain and higher in other organs), in order for the pressure to increase dramatically, removing the obstruction during infusion.

Figure 4C:
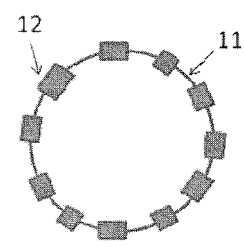

For this reason, the dialysis cavity casing, which encases said holes 10, preferably carries internal or even external protection 12, in order for the whole of the dialysis cavity not to increase/decrease in volume following changes in pressure, the only enlargement being that of the holes, thus in case of occlusion, a ratio of differential pressure to differential volume $\Delta P/\Delta V$ will be exceptionally high. This means that in utilizing the above preferred solution to the problem, the internal dialysis cavity pressure increases abruptly following a small infusion volume in case of occlusion, thus making the releasing over-infusion following the obstruction small in volume, and the pressure drop during unblocking rapid, without causing problems in the cranial soft tissue. Said protection 12 may preferably comprise flexible, non-elastic fibers circumferentially spiral or even cross-linked in order to prevent swelling of the dialysis cavity, and internal grid or spiral (FIG. 4a) or plastic of radial cross-section (FIG. 4b) to prevent shrinking on suction. Alternatively, inside said dialysis cavity, there can be a semi-hard plastic or elastic material of higher shore value or even thickness (FIG. 4c). To prevent occlusion, the holes may carry a biocompatible, hydrophobic coating, in order for the aqueous unblocking agents to pass through the hydrophobic holes only with a negative or positive pressure so as not to stick on them. Said holes 10 attain their largest size-diameter when in a swollen state, this diameter being smaller than that of the suction pipe 7, in order to prevent occlusion during passage to the waste collection bag.

In an alternative embodiment as shown in FIG. 5, the catheter preferably comprises one or more pressure sensors 13, 14, in particular two sensors with one 14 in the dialysis cavity interior measuring absolute pressure from 0.2 to 4 bar, for unblocking pressures (negative-suction up to 0.2-bar and positive-infusion up to 4 bar), and one 13 externally measuring the cerebral cavity pressure and covered with biocompatible elastic material, preferably parylene. The sensors can also be placed in a back-to-back configuration, one 13 looking outwards of the dialysis cavity while the other 14 looking inwards, endocranial pressure. Alternatively, an absolute pressure sensor 13 can be used in the outer casing of the dialysis cavity and additionally a differential sensor 14 in the inner casing of the dialysis cavity. It must be clarified at this stage that the pressure variation within the dialysis cavity 9 is small in case all of the holes are open (not blocked), as a communicating vessels configuration with the cerebral cavity and this is minimally dependent on the quantity of flow. Pressure variation increases due to the progressive clogging of the holes and simultaneous high flow rate, according to what is known in the hydraulic systems.

Pumping System Description

For forced circulation, the fluids exchanging system preferably uses a two-way pump 19 one for aspiration and the other for infusion. The system further includes the use of an alarm in case of an input obstruction which may indicate upstream occlusions including band tubing or blockages preventing fluid flow in the tubes. An alarm may also be triggered upon detection of excess air in the tubing indicating a leak which could lead to incorrect dosing of the patient. Such pumps are gear, vane, and piston pumps. Peristaltic and diaphragm pumps may be used in case the pipe/diaphragm mechanism has a large thickness and is made of silicone or TPE, so as to exhibit a smooth resilient tube recovery during the peristaltic movement. The aspiration pressure also represents an important need, it should drop down to 0.2 bar, in order to obtain a high unblocking force, feasible with a peristaltic tube with a 2 mm internal diameter/4 mm external diameter.

The difference in the precision of flow in two pumps is small, approximately about 5%, and it is balanced by the natural circulation-fluids regulation in the brain (500 ml/day) of the patient.

The flow in both pumps never stops, the lower flow being calculated (usually 1-10 ml/hr) in a way that it leaves no ground for tube/holes clogging-occlusion, according to what is known in infusion pumps with similar vein-catheter occlusion having flows called KVO—Keep Vein Open.

Figure 1:
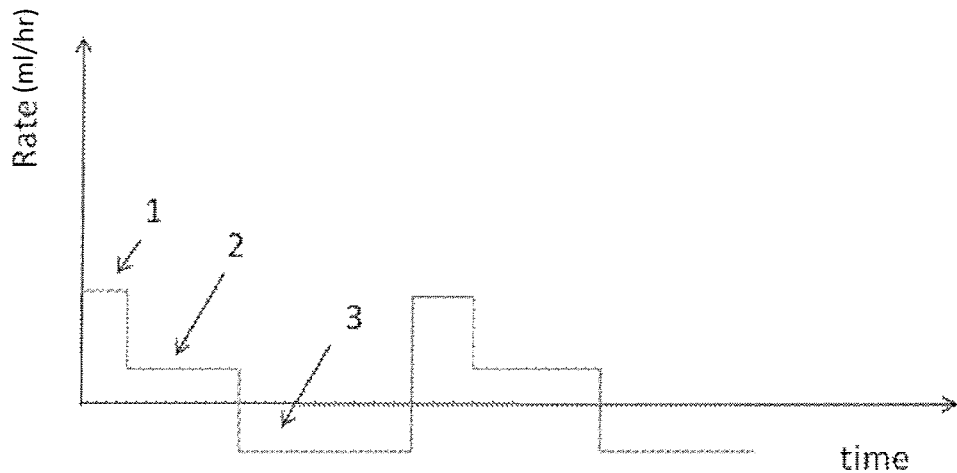
FIG. 1 shows the preferred flow/time graph, wherein the infusion flows are positive and the suction flow is negative.
Figure 2:
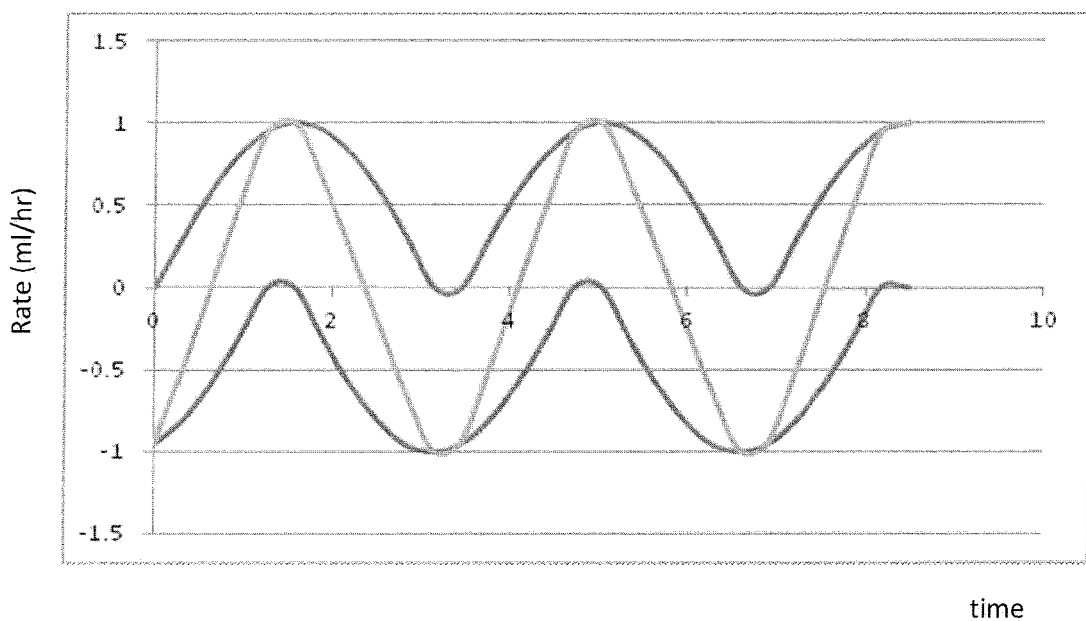
FIG. 2 shows the preferred flow/time graph for the sinusoidal reciprocating flow that facilitates dialysis.
Figure 3:
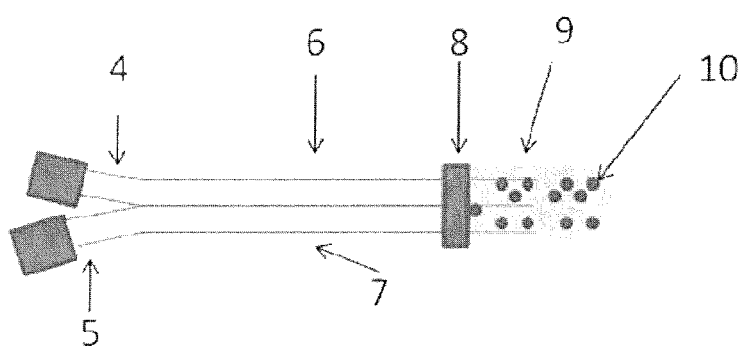
FIG. 3 shows an embodiment of a catheter pumping system without integrated pressure sensors.

The pumps in an example embodiment never work together, instead they are interchanging (discontinuous operation), and moving micro-volumes (FIG. 1) in order to prevent the short-circuiting from the input-output of viscous and non-dissolved means. In the non-viscous and soluble means a combination may exist of this flow with some continuous variation of simultaneous flows, allowing and encouraging the dissolution of the incoming and outgoing means (FIG. 2).

The variations in flow are continuous or intermittent, allowing the slight variation of the pressure curve in the dialysis cavity in case the holes are open. The intra-catheter pressure curve is used to predict or determine the partial (sufficient increase in the pressure variation) or total occlusion of the holes (excessive infusion pressure increase) and to trigger the corrective cleaning actions.

In case of only one sensor in the dialysis cavity 9 or external to it, with the holes not occluded the average pressure measurement and especially during aspiration 3 is considered to be the endocranial pressure.

The aspiration pump is connected so that its input is connected to the patient (catheter) and its output to the waste bag, while the infusion pump is connected normally, i.e. input connected to medicine bag with rinsing fluid.

In a first preferred embodiment the fluids exchanging protocol comprises flows in a three-step pattern according to FIG. 2 with a volume of 1 ml for each infusion 1,2 and the same for suction 3 thus ensuring the safe exchange of fluids in the cerebral cavity, the volume may be larger than 1 ml in other bodily cavities. The first-step infusion 1 is preferably injected using a high flow rate of 400-1000 ml/hr followed by infusion at a low flow rate of 1-10 ml/hr 2 with a calculated total volume by the pump of 1 ml. The two steps of course may become one or more than two. Suction follows at 1 ml 3 for a time equal or greater than the sum of the infusion times 1+2, while it also applies here that suction may exhibit an variation pattern or steps. The reasoning is that in order for the dialysis cavity holes to remain open the longest possible operating time at high pressure is needed (in case of occlusion) to achieve unblocking Infusion therefore should be rapid 1 at the onset of the infusion period, and continue with KVO 2 for maintaining the holes open in case they were not occluded. If pressure in the dialysis chamber 9 does not drop, (cleaning of holes), at the end of the infusion period, corrective infusion must be resumed until unblocking or a pressure-alarm triggering. The aspiration is continuous throughout period 3 in order to have a low flow rate inside the holes, and the continuation as well as the low flow rate prevent the built up of occluding barriers in the holes.

Protocol 1 example for gliomas (medicine, e.g. Carmustine): The doctor plans according to the treatment regime how much volume is needed per hour or during a 24 hour period and the pump calculates the infusion-suction period 1+2+3 and the suction flow 3 in ml/hr as well as the periods t1 and t2 using the system of equations. For example, for the 1 liter/24 hours planning, the calculation gives the following results: infusion-aspiration period 1+2+3 86.4 sec, infusion at 400 ml/hr for t1 1 8.123 sec, low flow rate infusion period t2 2 at 10 ml/hr equals 35.07 sec and suction flow rate 83.33 ml/hr for period t3 3 43.2 sec. The alarm pressure in dialysis chamber 9 is determined by the pressure capacity of the pump around 3-4 bar and the strength of the connectors and luer lock.

Protocol 2 example for hematomas (Aneurysm-subarachnoid hemorrhage/medicine, e.g. papaverine): The volume (ml) per hour or 24 hours and the suction flow rate (ml/hr) are programmed, and the pump calculates the times for the remaining phases 1 and 2.

In the case of two sensors 13, 14, the pump if during infusion measures a high internal (intra-catheter) pressure and a normal exterior (endocranial) one detects the existence of an obstruction in the holes 10 and continues the infusion until the obstruction is removed (sudden pressure drop) or until the maximum allowable safety pressure is reached. The additional volume used in the occlusion, is removed in the next stepwise infusion to restore volume and pressure balance.

When the endocranial pressure which is measured by the pressure sensor 13 in the dialysis cavity is reaching an alarm set point of the pump as programmed in the protocol, an alarm is triggered and an alarm sound is gradually increasing to alert personnel of a potential blockage or leak in the system and to allow them to fix the problem through implementation of a suction dose. The endocranial pressure is continuously displayed on the pump screen. The pressure development can be also displayed graphically. The pump displays also historical data on the intra-catheter pressure associated with any points of obstruction/occlusion.

For safety reasons the pump has itself an integrated pressure sensors (downstream occlusion detection) for the detection of any bending on the infusion tube, an empty infusion bag and catheter sensor(s) failure. The infusion and suction pumps sense also the obstruction of their input tubes (upstream occlusion). The sensors contained in the pump are capable of sensing air in the fluid pipeline, such as in the case of a leak or puncture which has occurred in one of the tubes or the catheter; an ultra sound sensor is a preferred sensor for this purpose.

In a second embodiment of the present invention, the minimum flow (both pumps work simultaneously as e.g., in FIG. 2) and the continuous variation of flow additional to the minimum flow, ensures the equilibrium of concentrations both inside and outside of the catheter due to dissolution. Dialysis is a chemical process and not a forced mechanical one. However, during use, there is risk of the catheter perforations becoming obstructed; to determine if this is the case, an infusion pump can be used to increase fluid flow through the system and to observe whether an increase in pressure occurs. If the intra-catheter pressure rises in relation to the respective endocranial, clogging of the holes has occurred and the infusion pump continues to provide increased flow until the pressure drops suddenly due to the removal of obstruction or until the alarm pressure level has been reached. It is a known fact that the pressure increases if the inflow into a space is higher than the outflow. The increased flow of the infusion pump at times helps by itself in the cleaning of the holes. The improvement of the system of this embodiment lies in the continuous flow variation of the suction pump, not creating a forced flow inwards which is the main cause of occlusion-clogging of the holes. We should clarify here a paradox, i.e., while the flow for a large part of the time is suction flow, the transport of medicine and other therapeutic substances to the outside is carried out continuously, because the dialysis phenomenon is not influenced by the reverse flow and the concentration equilibrium is extremely rapid.

A variant of this second embodiment is to have the two pumps working in two rectified sinusoidal flows as in FIG. 2, each pump goes with half a cycle from 0 to 0 within 180 degrees, with 90 degrees delay one pump/waveform from the other, hence there is always one of the two pumps working, stopping only in passing through zero, such that the resultant (internal triangular curve in FIG. 2) inward-outward triangular flow as a wave, with the same period as the pumps, assists the dialysis. This solution is a combination of pure dialysis and transport inwards-outwards. Moreover there is no such thing as complete halt in any of the pumps so that clogging is avoided, and due to a higher fluid circulation in the suction (hence higher waste dissolution in the tube), if the medicine is not expensive. Naturally, in case of clogging of the holes, at every 45 degrees interval we find increased and then minimum pressure alternately and then we increase the flow and volume of infusion according to the above, or in an early stage of clogging we narrow the sine of infusion (which presents a maximum in the minimum of suction) by increasing the flow to its maximum, usually 1000 ml/hr. The completion of the width of the period of infusion before and after is carried out with KYO. It is obvious that with a small $\Delta P/\Delta V$, pressure will rise to 2 bars easily, and it is maintained at this level with fluctuations until de-clogging occurs.

Protocol 3 example for medicines (Alzheimer/medicines, e.g. Exelon-liquid Aricept): The necessary volume is programmed per hour or day, and the pump calculates the period of sinusoidal flow for each pump and exchange of fluids. This protocol helps in achieving good solubility of the medicines in the cranial cavity.

Protocols 1, 2 and 3 may have the option of selecting a volume per step larger than 1 ml, for other bodily cavities that do not present the problem of hypertension like the cerebral cavity does, and hence have decreased needs for pressure monitoring.

It should mentioned that in the present embodiments the high value of $\Delta P/\Delta V$ consequently results in a high circulation of fluids inwards as well as outwards the holes 10, rendering unnecessary in practice the special process of unblocking; in which case 90% of the one ml volume passes through the holes and inflates them and only 10% inflates the dialysis cavity itself, which is not at all evident in the prior art.

Pressure as a waveform can be processed by the pump controller mathematically, implementing various algorithms and techniques as digital filters, wavelets, Goertzel coefficients, etc., to predict the oncoming clogging. This possibility offers the advantage of performing cleaning of the clogging using a lower pressure than that used in heavy clogging. It is to be understood that the intra-catheter pressure presents a higher variation with each new clogging of even only one hole, and continues increasing up to the total clogging of the catheter.

The use of the second pressure sensor on the exterior part, or in a notch on the catheter body, in order to measure the pressure of the cerebral cavity, is auxiliary to the process, when the limit is reached an alarm sounds, at a lower level the doctor may program the automatic pressure adjustment from the pump using infusion or aspiration, and in doing so the pump takes into consideration both measurements inside and outside for safety reasons, these measurements should only differ marginally.

In carrying out rinsing a portion of the brain or of another part of the body which has been operated on, rinsing being a therapeutic process on its own through the removal of damaging residual surgical materials or hematomas, the system can be used with circulating fluid containing cleaning liquid plus medicine in case the medicine is cheap. For expensive medicines a third pump can be used, with or without another separate tube (Lumen) and in this case its volume in time is subtracted from the classic infusion pump for rinsing or active valves can be used (e.g., those of the Lee Company) in combination with passive check valves. The different embodiments and protocols of this disclosure may be combined in the pump electronic control as different infusion modes/profiles depending on the type of treatment, as well as the allowable pressures.

The fluids exchanging system of the present disclosure can be also used in other bodily cavities, with a corresponding cost reduction, where the pressure sensors may be replaced by corresponding ones from the general trade, e.g., the ones supplied by the company Biosensors International, Accutrans model 18, and said protection for the holes may be replaced by a simple homogeneous elastic membrane 11 bearing holes 10 without protection 12. In an even cheaper solution, pressure is measured by the pump occlusion detector, which as in the previous occasions with sensors, serves also as a safety feature. The catheter may have an introducer made of metal wire e.g., super elastic Nitinol, inside a tube, i.e. one of those for input-output, which is removed after the successful surgical insertion. The catheter may preferably have at the tip one or more, and at various points, radio- or ultrasound-visible marks, in order for the catheter placement to be visible in X-rays or ultrasound. The catheter may carry an external coating comprising a lubricating biocompatible substance for easy insertion during the surgical procedure, and internally in the suction tube to prevent blockage by the agglomerating particles.

The catheter can have the pipes for infusion 6 and suction 7 as well as measurement (cables) parallel in an multilumen array leading to said dialysis cavity using circumferential bonding resistant to high pressure without leaking, or coaxially implementing Y splitting of the tubes as is well known in catheters or a combination of those e.g., measuring and infusion tubes inside a flexible polyurethane tube continuing as the pump suction pipe up to the splitting point.

The catheter may also carry external sensors measuring the treatment results (therapeutic and side effects), the sensors passing their signals independently, or through a cable common to that of the pressure sensors.

The catheter is used in the operating room, whereas its connection to the pump is done in a separate space. In order to avoid errors, the infusion and suction tubes 4, 5 each are provided with a biased connector or two Luer locks 15, 16 as shown in FIG. 5, wherein the lock 15 may be a male lock and the lock 16 may be a female lock. As further shown in FIG. 5, the catheter is additionally provided with an optical or electrical sensor signal connector 17.

FIG. 6 shows an assembly including an external pressure sensor 18, a double pump 19, a bag 20 for medicine, a bag 21 for waste and a signal cable 22, wherein the catheter is connected with the lock of one of its tubes to the external pressure sensor 18 and with the lock of its other tube via a connector directly to the double pump 19.

The tubing from the pumps up to the catheter should be flexible but not extendable; hence a piping of 3 to 4 mm in diameter in use with the common infusion pumps is not acceptable, only tubing with a small internal diameter made of relatively hard and inelastic material that does not impede flow in case of bending (anti kinking).

The reason is the maximization of the aforementioned $\Delta P/\Delta V$, in order for the system as a whole, consisting of pump-tubing-catheter to have a $\Delta P/\Delta V$ much higher than 2 bar/ml, that is to say a pressure capable of carrying out cleaning without the over-infusion volume after unblocking exceeding the medically acceptable limit of 1 ml for the brain, because the inelastic tubing will relief overpressure very fast without vibrations.

The invention claimed is:

1. A system for exchanging fluids in patients, comprising:
an infusion pumping system;
an aspiration pump; and
an implantable catheter comprising a perforated dialysis cavity communicating with infusion and aspiration tubes in a communicating vessels manner and including holes in a cavity casing, wherein the holes of said perforated dialysis cavity are elastic and configured to pressure dilate and the cavity casing includes an internal protector configured to maintain the volume of the perforated dialysis cavity.

2. A system for exchanging fluids in patients according to claim 1, wherein a body of the dialysis cavity is manufactured for a high ratio of differential pressure to differential volume ($\Delta P/\Delta V$), exhibiting low swelling in pressure and low shrinkage in vacuum.

3. A system for exchanging fluids in patients according to claim 1, wherein the infusion and aspiration pumps have protocols supporting continuous flow.

4. A system for exchanging fluids in patients according to claim 1, wherein an infusion flow rate (ml/hr) at periodical time segments is higher than an aspiration flow rate, or even at corresponding segments wherein the aspiration flow rate is higher than the infusion flow rate in order to generate a forced flow out of or into the dialysis cavity and to clean the holes.

5. A system for exchanging fluids in patients according to claim 1, wherein the exchange of fluids in a bodily cavity is carried out by combining dialysis and forced circulation, wherein the fluid is being removed from the body or infused into the body of a patient at different times.

6. A system for exchanging fluids in patients according to claim 1, comprising a pressure sensor, wherein continuous measurement of pressure in the dialysis cavity aids in prediction of a partial or total occlusion of communicating holes of the dialysis cavity and triggers a cleaning protocol for the holes.

7. A system for exchanging fluids in patients according to claim 1, comprising a pressure sensor outside the dialysis cavity for making pressure comparisons inside as well as outside of the dialysis cavity and triggering an alarm to alert treating personnel in case of undesirable resulted pressure comparisons.

8. A system for exchanging fluids in patients according to claim 1, wherein the catheter carries a lubricating coating on catheter interior and exterior tubes to prevent adhesion of particles onto tube surfaces.

9. A system for exchanging fluids in patients according to claim 1, wherein the infusion and aspiration pumps have protocols supporting discontinuous or intermittent flow.

10. A system for exchanging fluids in patients, comprising:
an infusion pumping system;
an aspiration pump; and an implantable catheter comprising a perforated dialysis cavity communicating with infusion and aspiration tubes in a communicating vessels manner and including holes, wherein:

the holes of said perforated cavity are elastic and configured to pressure dilate such that the circumference of each of the holes is variable; and a body of the dialysis cavity is configured for a high ratio of differential pressure to differential volume ($\Delta P/\Delta V$), exhibiting low swelling in pressure and low shrinkage in vacuum.

11. A system for exchanging fluids in patients according to claim 10, wherein the exchange of fluids in a bodily cavity is carried out by combining dialysis and forced circulation, wherein the fluid is being removed from the body or infused into the body of a patient at different times.

12. A system for exchanging fluids in patients according to claim 10, comprising a pressure sensor, wherein continuous measurement of pressure in the dialysis cavity aids in prediction of a partial or total occlusion of communicating holes of the dialysis cavity and triggers a cleaning protocol for the holes.

13. A system for exchanging fluids in patients according to claim 10, wherein the implantable catheter includes a cavity casing comprising an internal protector configured to maintain the volume of the perforated dialysis cavity.

14. A system for exchanging fluids in patients, comprising:
an infusion pumping system;
an aspiration pump; and
an implantable catheter comprising a perforated dialysis cavity communicating with infusion and aspiration tubes in a communicating vessels manner and including holes, wherein:

the holes of said perforated cavity are elastic and configured to pressure-dilate in order to release entrapped material fragments and remove said fragments using fluid pressure either infusion pressure or aspiration pressure.

15. A system for exchanging fluids in patients according to claim 14, wherein a body of the dialysis cavity is fabricated for a high ratio of differential pressure to differential volume ($\Delta P/\Delta V$), exhibiting low swelling in pressure and low shrinkage in vacuum.

16. A system for exchanging fluids in patients according to claim 14, wherein the exchange of fluids in a bodily cavity is carried out by combining dialysis and forced circulation, wherein the fluid is being removed from the body or infused into the body of a patient at different times.

17. A system for exchanging fluids in patients according to claim 14, comprising a pressure sensor, wherein continuous measurement of pressure in the dialysis cavity aids in prediction of a partial or total occlusion of communicating holes of the dialysis cavity and triggers a cleaning protocol for the holes.

18. A system for exchanging fluids in patients according to claim 14, wherein the implantable catheter includes a cavity casing comprising an internal protector configured to maintain the volume of the perforated dialysis cavity.

* * * * *